United States Patent [19]
Capuano

[11] Patent Number: 5,454,258
[45] Date of Patent: Oct. 3, 1995

[54] BROAD RANGE MOISTURE ANALYZER AND METHOD

[75] Inventor: Italo A. Capuano, Orange, Conn.

[73] Assignee: Olin Corporation, Cheshire, Conn.

[21] Appl. No.: 239,804

[22] Filed: May 9, 1994

[51] Int. Cl.⁶ .................................................. G01N 33/00
[52] U.S. Cl. .................... 73/61.43; 73/61.41; 73/64.56
[58] Field of Search ................. 73/61.41, 61.43, 73/64.56

[56] References Cited

U.S. PATENT DOCUMENTS

| | | | |
|---|---|---|---|
| 3,077,105 | 2/1963 | Ohlheiser | 73/61.43 |
| 3,799,846 | 3/1974 | Capuano | 204/1 |
| 3,971,248 | 7/1976 | Christensen | 73/61.43 |
| 4,112,744 | 9/1978 | Tassano | 73/61.43 |
| 4,745,795 | 5/1988 | Emmert | 73/61.41 |
| 5,001,067 | 3/1991 | Coleman et al. | 73/61.43 |
| 5,088,315 | 2/1992 | Johnson | 73/23.2 |
| 5,157,339 | 10/1992 | Scott et al. | 73/61.43 |
| 5,157,961 | 10/1992 | Bialsky et al. | 73/61.41 |
| 5,226,950 | 7/1993 | Yu | 73/61.43 |
| 5,294,378 | 3/1994 | Succi et al. | 261/130 |

Primary Examiner—Richard E. Chilcot, Jr.
Assistant Examiner—Eric S. McCall
Attorney, Agent, or Firm—Dale Lynn Carlson

[57] ABSTRACT

An analyzer and method for detecting and measuring the water content of a fluid sample in which a stream of the fluid sample is mixed with and diluted by a dry gas to lower the water content of the resulting sample stream. The resulting sample stream is passed through a moisture detector which provides an electrical signal indicative of the amount of water in the diluted sample.

28 Claims, 3 Drawing Sheets

BROAD RANGE MOISTURE ANALYZER AND METHOD

BACKGROUND OF THE INVENTION

1. Field of the Invention

This invention relates generally to a method and analyzer for detecting and measuring the amount of water (moisture) in a fluid. More particularly, this invention relates to a method and analyzer for detecting and measuring water in chemical process fluid streams over a wide range of water concentrations.

2. Background

Many chemical reactions leading to the production of organic products such as isocyanates, polyethers, and others, should be conducted in the absence of water to prevent loss of yields, products contamination, and the possible damage to equipment due to the formation of solids. Additionally, in many cases where acidic materials such as hydrogen chloride, phosgene and chlorine are used or formed in a chemical process, introduction of water from external sources such as a heat exchanger or humid air must be excluded as water could react or ionize such species to form extremely corrosive conditions which could be detrimental to plant equipment and operation.

In order to assess if the presence of water in a process stream has reached a serious proportion and corrective action should be taken, it is desirable that a suitable analyzer be available for detecting the presence of water and providing a indication of the concentration thereof. However, to be effective with various chemical processes, the analyzer must be capable of measuring a wide range of concentrations, from a few parts-per-million (ppm) to percentage levels.

Known commercial analyzers available at the present time are not capable as a unit to perform a wide range of water analysis. Conventional spectroscopic analyzers, such as near-infrared detectors, are neither suitable for the measurement of very low moisture concentrations (0–50 ppm), nor for concentrations higher than 1000 ppm of water. Such analyzers are not capable of detecting the low concentrations of water, and at the higher concentrations, the water tends to produce emulsions with organic systems such as benzene, chlorobenzene, toluene and the like, which are opaque to light, and render it impossible to make measurements. Electrochemical water analyzers, such as coulometric, amperometric, and dielectric constant analyzers, are suitable for low water concentration measurements (0–1000 ppm), but are not suitable for analysis when the concentration is above 1000 ppm due to lack of measurement linearity.

SUMMARY OF THE INVENTION

In view of the above, it is an object of the present invention to provide an improved method and analyzer for detecting and measuring the concentration of water in a fluid.

A more specific object of the present invention is to provide an improved method and analyzer for detecting and measuring the concentration of water in a fluid which is capable of operating over a wide range of water concentrations.

Yet another object of the present invention is to provide an improved method and analyzer detector which is capable of detecting and measuring the concentration of water in a liquid chemical process stream over a wide range of water concentrations.

Still another object of the present invention is to provide of a method and analyzer which is capable of detecting and measuring the concentration of water in an organic vapor chemical process stream over a wide range of concentrations.

These and other objects and advantages of the present invention may be achieved through the provision of an analyzer for detecting and measuring the water content of a fluid sample which comprises means for gathering a stream of the fluid sample, diluting means for diluting the sample with a water-free fluid, and moisture detection means for detecting the presence of water in the diluted sample and providing an electrical signal indicative of the amount of water in the sample.

A method in accordance with the present invention may comprise providing a stream of a fluid sample, diluting the stream of fluid sample with a water-free fluid, and detecting the presence of water in the diluted sample by means of a moisture detector and providing an electrical signal indicative of the amount of water in the sample.

BRIEF DESCRIPTION OF THE DRAWINGS

The objects and advantages of the present invention will become more apparent by reference to the following detailed description and to the accompanying drawings in which.

DETAILED DESCRIPTION

Figure 1:
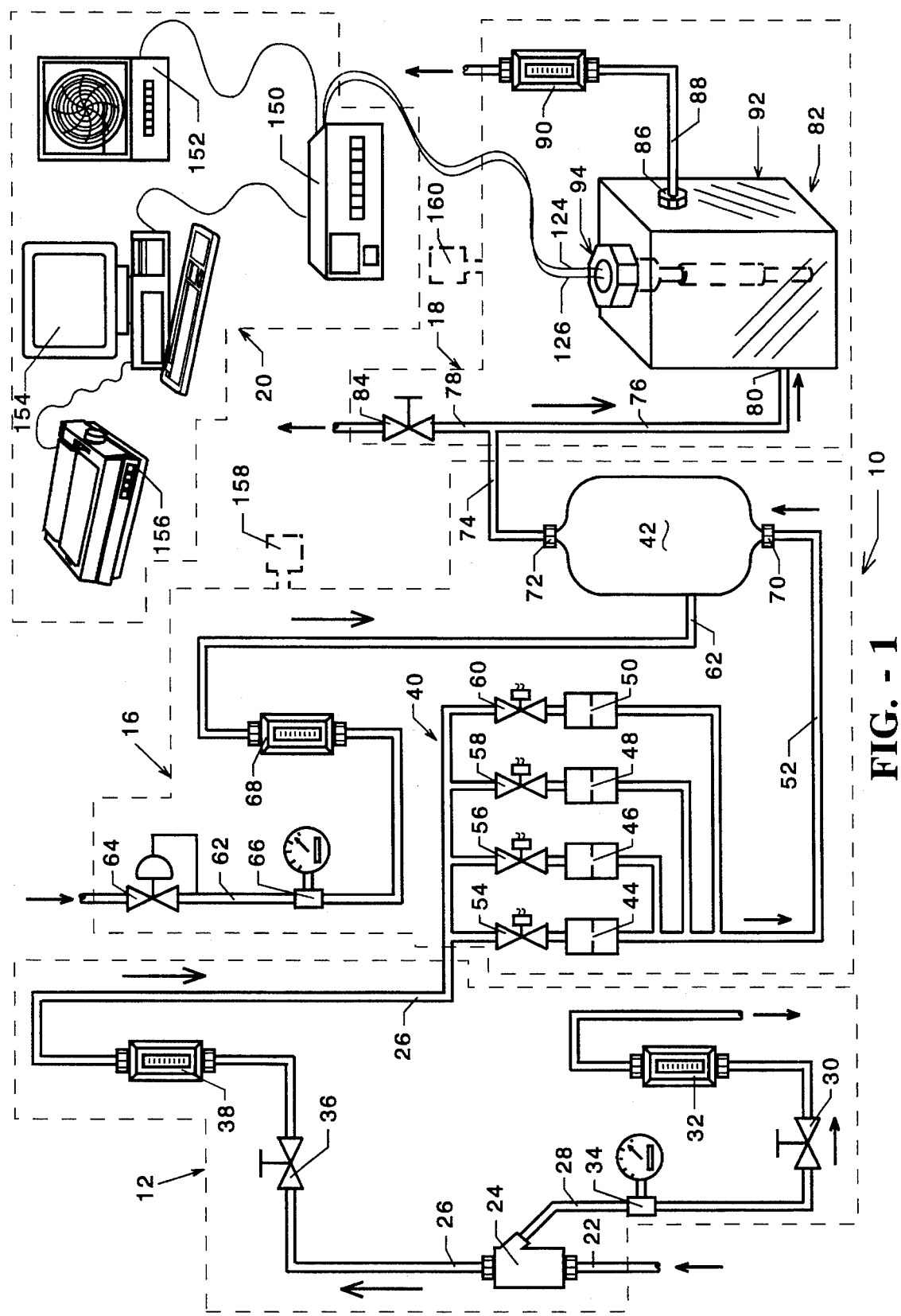
FIG. 1 is a schematic diagram of an analyzer embodying the principals of the present invention and which is designed for sampling a chemical process organic vapor stream.

Referring to the drawings and particularly to FIG. 1, there is shown an analyzer 10 which is capable of detecting moisture or water in a stream of vapor, particularly an organic vapor. In general, the analyzer 10 of FIG. 1 comprises a sampling means 12 for providing a sample of a process gas or vapor, diluting means 16 for diluting the sample, moisture detecting means 18 for detecting the moisture in the sample, and control and output means 20 for controlling the operation of the analyzer and providing means for converting the signals from the detecting means 18 into output data.

More specifically, the vapor to be sampled enters the sampling means 12 of the analyzer 10 through an input line 22 which is attached to a source of the vapor to be sampled. The sample may be taken from any convenient location in the chemical process stream at which point in the process the determination of the moisture content is of interest. The input line 22 is connected to a filter 24 such as a Y-strainer which serves to remove any solid particles from the incoming vapor sample.

The filter 24 may be of any appropriate type which is capable of preventing passage of the solid particles into the vapor sample incoming flow line 26. A relatively large portion of the incoming vapor to the filter 24 is returned unfiltered back to the chemical stream through a vapor return line 28. A flow restrictor 30 is provided in the vapor return line 28 with a flow meter 32 positioned in the line 28 downstream of the restrictor 30 and a pressure gauge 34 positioned in the line 28 upstream of the restrictor 30. The flow restrictor 30 may be of any suitable type capable of controlling the flow of the vapor therethrough and thus the pressure of the vapor upstream of the restrictor. A needle-type flow restricting valve is an example of a suitable type of restrictor 30. The pressure gauge 34 provides an indication of the pressure of the sample while the flowmeter 32 serves to verify movement of the vapor sample through the line 28.

The filtered vapor sample leaves the filter 24 through the sample incoming flow line 26 where it passes to the diluting means 16. The sample incoming flow line 26 has a flow restrictor 36 therein, similar to flow restrictor 30, and a flow meter 38 downstream thereof as shown in FIG. 1. The flow restrictor 36 and flow meter 38 are used to control and monitor the flow of the vapor sample to the dilution means 16.

The dilution means 16 includes a computer-selective variable flow rate path network 40 which provides a means for selecting different flow rates of the incoming vapor stream to provide for the proper dilution-flow variations. The dilution means 16 also includes a mixing chamber 42 in which the vapor sample is mixed with and diluted by an incoming water-free fluid such as a dry gas.

The variable flow rate path network 40 comprises a series of flow restrictors such as orifices 44, 46, 48 and 50, each of which is of a different size whereby the flow rate of the vapor sample through each of the orifices 44, 46, 48 and 50 is different. The orifices 44, 46, 48 and 50 are located in parallel between the incoming sample flow line 26 and a vapor sample line 52 to the mixing chamber 42.

An on-off valve 54, 56, 58 and 60 is associated with each of orifices 44, 46, 48 and 50 respectively. The valves 54, 56, 58 and 60 are connected between the line 26 and their respective orifices 44, 46, 48 and 50 such that the vapor sample stream coming from the filter 24 must pass through one of the valves 54, 56, 58 or 60 and its associated orifice 44, 46, 48 or 50 before passing to the vapor sample line 52 to the mixing chamber 42. Each of the valves 54, 56, 58 and 60 may be any suitable type of an electrically actuated on-off valve such as a solenoid actuated, pneumatically operated valve, the operation of which is controlled by electrical signals from the control and output means 20.

A water-free fluid, preferably a dry gas such as dry nitrogen or dry air, is introduced into the system by means of an incoming dry gas line 62. The dry gas line 62 is connected at its incoming end to a suitable source of the dry gas such as that which may be readily available on site at the plant, or may be supplied by a separate tank. The other end of the gas line 62 is connected to the mixing chamber 42. The line 62 includes a pressure regulator 64, and a pressure gauge 66 and flow meter 68, both of which are positioned downstream of the pressure regulator 64. The pressure regulator 64 serves to control the pressure of the incoming dry gas while the pressure gauge 66 and flow meter 68 provide a means to monitor the gas pressure and flow respectively of the incoming dry gas.

The line 52 from the variable flow rate path network 40 is connected to an inlet 70 at the bottom of the mixing chamber 42 such that the incoming vapor sample and the dry gas both meet in the mixing chamber 42 and are dynamically mixed. The mixing chamber 42 allows the two gas streams to mix uniformly with the result that the dry gas dilutes the inorganic vapor stream and lowers the water content of the resulting sample stream.

After dynamically mixing in the mixing chamber 42, the resulting sample stream exits the mixing chamber 42 through an outlet 72 to which is connected one end of a sample flow line 74, and flows in the line 74 to the moisture detecting means 18. The sample flow line 74 branches at its other end into a sample input line 76 and a vent line 78. The sample input line 76 is connected to an inlet 80 of a moisture detecting cell 82 of the moisture detecting means 18. The vent line 78 is vented to the atmosphere, or to a plant scrubber (not shown) with a pressure lower than that of the incoming sample in input line 22, through an adjustable flow restrictor 84 which serves to provide a back pressure in the system allowing for greater control of the flow of the sample stream through the input line 78 and into the moisture detecting cell 82. An outlet 86 of the moisture detecting cell 82 has a vent line 88 connected thereto which is vented to the atmosphere or to a plant scrubber as described above through a flow meter 90. The flow meter 90 is used to monitor the flow of the sample through the moisture detecting cell 82.

The moisture detecting cell 82 and its operation may be of the type described in U.S. Pat. No. 3,799,846, issued Mar. 26, 1974 to I. A. Capuano and entitled "Moisture Analysis Method", the disclosure of which is incorporated herein by reference in its entirety. While reference may be made to that patent for a detailed explanation of the construction and operation of a suitable moisture detecting cell, briefly, the cell is an electrolytic cell and utilizes closely spaced electrodes coated with a film of a hygroscopic material which is substantially non-conductive electrically and non-reactive with the material being sampled, but reactive with water to form an electrically conductive substance. The electrically conductive substance, in turn, upon the application of a potential difference (voltage) across the electrodes, decomposes electrolytically into the elements of water with the regeneration of the hygroscopic material. The resulting electrolysis current is proportional to the water content in the sample being tested.

Figure 3:
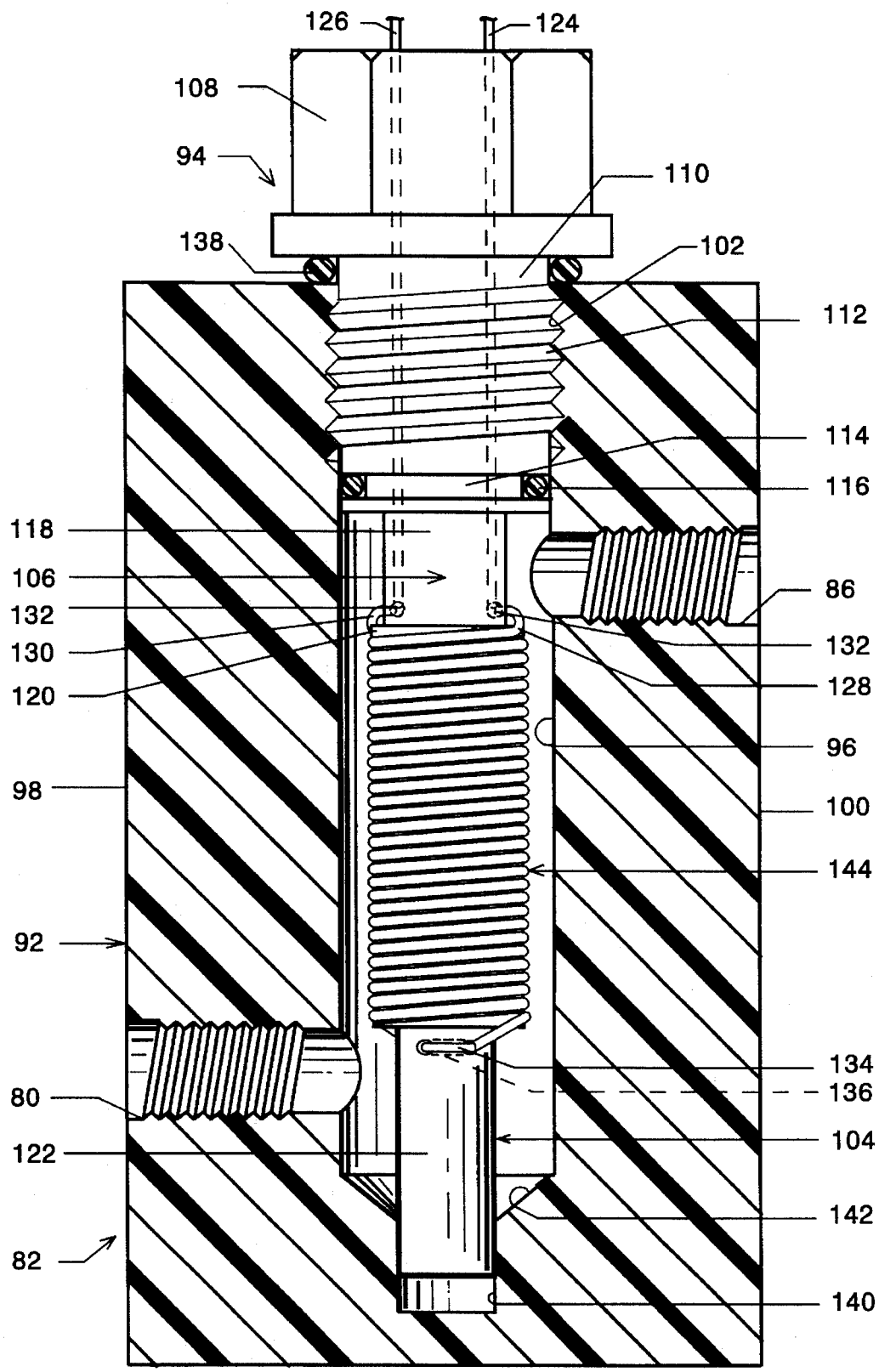
FIG. 3 is an elevational view, partially in section, of a an electrochemical sensor cell used in the analyzer of the present invention.

FIG. 3 shows an example of a suitable moisture detecting cell 82 of the type referred to in the aforesaid U.S. Pat. No. 3,799,846 and capable of being used with the present invention. The cell 82 includes a cell block 92 and a rod-like sensor 94 extending into an axial bore 96 in the cell block 92.

The cell block 92 has a rectangular cross-section with the axial bore 96 extending thereinto from its top surface and into which the rod-like sensor 94 extends. The cell block 92 includes the inlet 80, which may be internally threaded to provide for a connection with the inlet line 76, positioned in the lower portion of one of its side walls 98. The upper portion of the side wall 100 of the cell block 82 opposite the side wall 98 is provided with the outlet 86, which may be threaded to provide for a connection with the vent line 88. The inlet 80 and outlet 86 communicate with the axial bore 96 in the cell block 92 which has a threaded upper portion 102 as shown. Although the inlet 80 and outlet 86 are shown as being on opposing side walls of the cell block 82, alternatively, the inlet 80 and outlet 86 may both be in the same side wall.

The sensor 94 includes an electrode holding member 104 having an elongated rod portion 106 provided with a cap or head portion 108 at one end thereof. The electrode holding member 104, as well as the cell block 92, may be fabricated from a suitable dielectric material. The cell block 92 is preferably fabricated from clear polymethylmethacrylate which will permit the visual inspection of the electrodes. The electrode holding member 104 is preferably fabricated from polyethylene which is an effective insulator and has good wettability and absorption characteristics for the hygroscopic material. Other plastics such as polyvinyl chloride, polymethylmethacrylates and polystyrene are also suitable.

The rod portion 106 includes an enlarged diameter upper segment 110 adjacent the cap or head portion 108, a portion of the length of which has raised threads 112 thereon. The diameter of this segment 94 is such that the threads 112 will engage with the threads 102 of the upper portion of the bore 96 in the cell block 92 to secure the sensor 104 in the cell block 92. A lower unthreaded portion of the enlarged diameter segment 110 has a circumferentially extending groove 114 therein in which is mounted an 0-ring 116 which is in sealing engagement with the wall of the bore 96.

The rod portion 106 also includes a reduced diameter first intermediate segment 118, an enlarged diameter second intermediate segment 120, and a reduced diameter end segment 122. The enlarged diameter second intermediate segment 120 of the rod portion 104 has a diameter smaller than the diameter of the bore 96 in the cell block 92 and is provided with double threads running substantially the entire length of the segment.

Two spaced lead wires 124 and 126 extend down through bores (not shown for the sake of clarity) in the cap portion 108 and the enlarged diameter upper segment 110 and reduced first intermediate section 118 of the rod portion 104. Two electrode wires 128 and 130 are wound around the enlarged diameter second intermediate section 122 in the threads thereof in parallel fashion, with each wire being in a different one of the double threads. The upper end of each of the electrode wires 128 and 130 is turned into an appropriate opening in the wall of the reduced diameter first intermediate section 118 of the rod portion 106 and is attached to its associated lead wire 124 and 126 respectively by spot welding or the like as indicated at 132. The lower end 134 of each of the electrode wires 128 and 130 adjacent the reduced diameter end segment 122. of the rod portion 106 is secured to the end segment 122 of the rod portion 106 by any suitable means such as by looping the end 134 through a transverse bore 136 in reduced end segment 122 and knotting the end 134 to itself.

The lead wires 124 and 126 may be of any suitable electrically conductive material, although platinum is preferred because of possible corrosion. The electrode wires 128 and 130 are preferably platinum, but any of the platinum group metals or their alloys may be used.

The rod portion 106 of the sensor 94 is threaded into the bore 96 of the cell block 92. An O-ring 138 is compressed between the bottom of the cap portion 108 and the upper surface of the cell block 92 to form a gas-tight seal between the sensor 94 and the cell block 92. The reduced diameter end portion 122 of the rod portion 106 of the sensor 94 is snugly received within a reduced portion 140 of the bore 96 at the bottom of the cell block 92 to provide a firm assembly. The entrance portion 142 to the reduced portion 140 of the bore 96 is conical to aid in the insertion of the sensor 94 into the cell block 92.

The length of the enlarged diameter intermediate segment 120 of the rod portion 106 of the sensor 94 having the exposed platinum electrode wires 128 and 130 wound in the double threads forms an electrode area 144 which is provided with a film of a hygroscopic material. The hygroscopic material is substantially non-conducting and non-reactive with the fluid being sampled, but reacts with water to form an electrically conducting substance. When an electrical voltage differential is applied across the electrodes, the electrically conducting substance decomposes into the elements of water with the regeneration of the hygroscopic material.

Hygroscopic materials suitable for use as the film on the sensor include phosphorus pentoxide, sodium hydroxide, potassium carbonate, potassium hydroxide, potassium metaphosphate and silicic acid, it being understood that the material selected should be one that is non-reactive with the components of the fluid being sampled except for water. Phosphorous pentoxide is eminently suited for most sample materials and is preferred.

By way of example, when using a phosphorous pentoxide film on the two electrodes, the application of a potential difference across the electrodes causes the cell to operate on the following electrochemical principal:

$$P_2O_5 + 3H_2O \longrightarrow 2H_3PO_4$$

and $$2H_3PO_4 + \text{electricity} \xrightarrow{e^-} 1\,\tfrac{1}{2}\,O_2 + 3H_2 + P_2O_5$$

with the electrolytic current produced in the measurement being proportional to the water or moisture concentration in the sample.

The current produced by the electrolysis in the moisture detecting cell 82 is carried by the pair of lead wires 124 and 126 to the control and output means 20. The control and output means 20 may include a controller-microprocessor unit 150 to which the lead wires 124 and 126 are connected. The controller-microprocessor unit 150 may include an appropriate power source, preferably a 75 volt D.C. regulated power supply, as well as circuitry for converting the current signal for output to a recorder 152 such as a chart recorder. The control and output means 20 may also include a computer 154 connected to the controller 150 for calculation of the data and a printer 156 for outputting the data.

The dilution means 16, including the variable flow rate path network 40, mixing chamber 42 and associated piping, and the moisture detecting means 18, including the moisture detecting cell 82 and its associating piping, are each house in a thermostated unit, or together in a single thermostated unit. The thermostated units serve to maintain the sample and dry gas passing though the dilution means 18 and moisture detecting means 18 at a constant temperature. The units may be thermostated by the use of hot air heaters shown schematically at 158 and 160, although other types of heaters such as electrical heaters or the like may be used. By maintaining a constant temperature, variations in the flow rate of the sample and the dry gas due to variations in the temperature will be prevented.

In the operation of the device of FIG. 1, which is designed for the monitoring of moisture in an organic vapor stream, the incoming vapor sample is filtered by the filter 24 and passes into the variable flow rate path network 40. The variable flow rate path network 40 provides the proper flow rate of the vapor stream to the mixing chamber 42 to provide for the proper dilution of the vapor sample in the mixing chamber 42. In the network 40, the vapor stream passes through one of the valves 54, 56, 58 or 60, and its associated orifice 44, 46, 48 or 50 as determined by the microprocessor to provide the desired flow rate of the vapor sample to the mixing chamber 42. In the mixing chamber 42, the vapor sample is mixed with and diluted by a dry gas which is supplied to the mixing chamber 42 at a constant pressure and flow rate as controlled by the pressure regulator 64. Thus as the flow rates to the mixing chamber 42 of both the vapor stream and the diluting dry gas are known, the amount of dilution of the vapor sample by the dry gas is known.

The resulting diluted sample stream leaves the mixing chamber 42 and passes through lines 74 and 76 and enters the moisture detecting cell 82. The diluted vapor stream passes into the cell 82, bathing the electrode area 144 thereof. Any water in the sample reacts with the phosphorous pentoxide film as described above, producing a current proportional to the amount of water reacting with the film. The current signal is carried to the controller-microprocessor unit 150 by the lead wires 124 and 126 where the signal is converted to a form for outputting to the recorder 152 and computer 154 for further processing.

Assuming that the valves 54, 56, 58 and 60 of the fluid flow path network are initially set so that the valve 54 associated with the largest orifice 44 is open, with the remaining valves 56, 58 and 60 closed, the flow rate of the vapor stream to the mixing chamber 42 will be at its greatest rate. As the flow rate of the dry gas to the mixing chamber 42 is constant, the resulting sample stream leaving the mixing chamber will be the least diluted, thus permitting the analysis of vapor streams having the lowest level of water concentrations. If the controller 150 receives a signal from the moisture detection cell 82 that is incapable of conversion into a reading of the water content because the water content of the sample stream flowing through the cell is too high, the microprocessor will cause one of the other valves 56, 58 or 60 associated with a reduced size orifice to open and close valve 54, thereby reducing the flow of the vapor to the mixing chamber 42. With a reduced flow rate of the vapor stream to the mixing chamber 42, when the reduced flow rate vapor stream is mixed with the same constant flow of the dry gas, there is a greater dilution of the vapor stream, and the water content of the resulting diluted sample stream passing to the cell 82 is thus lowered. As the orifices 44, 46,48 and 50 are of decreasing size, thus providing for a decreasing amount of flow of the vapor sample stream to the mixing chamber 42 when the sample passes therethrough, the controller 150 can provide the proper path through the variable flow path network 40 to provide the proper flow rate of vapor sample stream to the mixing chamber 42 so that when diluted, the water content of the resulting mixture of dry gas and vapor is within a range that can be accurately detected. The computer 154 may be programmed so that the proportion of dry gas to vapor is known for each flow path (orifice) through the network 40 so that the actual concentration of water in the vapor stream may be calculated using the proper sample dilution factor.

The moisture detecting cell 82 of the type described herein is capable of operating linearly, and thus providing an accurate signal proportional to the actual water content, at water concentrations of up to 200 ppm. The analyzer 10 may thus be initially calibrated by using a laboratory sample of a gas having a known water content of below 200 ppm while directing the laboratory sample through the flow path containing the largest orifice 44. The flow rate of the diluent dry gas to the mixing chamber 42 is set to be constant.

By way of example, the flow rate of the sample to the mixing chamber 42 through the largest orifice 44 may be 3000 milliliters per minute (ml/min) with the flow rate to the mixing chamber 42 of the diluent dry gas maintained constant at 2000 ml/min. The adjustable flow restrictor 84 in the vent line 78 should be set to ensure that the flow through the moisture detector cell 82 is at or above the rate at which the cell 82 becomes relatively insensitive to flow rates, which in the case of the cell 82 described herein is about 1000 ml/min and above.

With the analyzer calibrated to provide an accurate readout of the moisture content below 200 ppm with flow through the largest orifice 44, the computer may be programmed with an appropriate factor to provide for an accurate readout when the other orifices 46, 48 and 50 are used. For example, the second largest orifice 46 may provide for a sample flow rate of 300 ml/min, the third largest orifice 48 for a sample flow rate of 100 mil/min and the smallest orifice 50 for a flow rate of 60 mil/min resulting in a flow of the combined sample and diluent dry gas through the moisture detecting cell 82 of 2300 ml/min, 2100 mil/min and 2060 ml/min respectively. With these flow rates, the computer may be programmed to multiply the output from the moisture detecting cell 82 by a factor of 10, 30 or 50 depending upon whether orifice 46, 48 05 50, respectively, is being used, to calculate the exact moisture content of the sample.

With the arrangement as described herein, the analyzer 10 can accurately detect moisture content of up to 200 ppm when there is flow through the largest orifice 44, up to 2000 when there is flow through orifice 46, up to 6000 ppm with flow through the orifice 48 and up to 10,000 when there is flow through the smallest orifice 50. The computer is programmed so that the orifice selected is the one which will result in the least amount of dilution, but still permit an accurate reading by the moisture detecting cell 82. This will ensure that the most sensitive scale will be used, resulting in the most precise measurements for a given water concentration.

Figure 2:
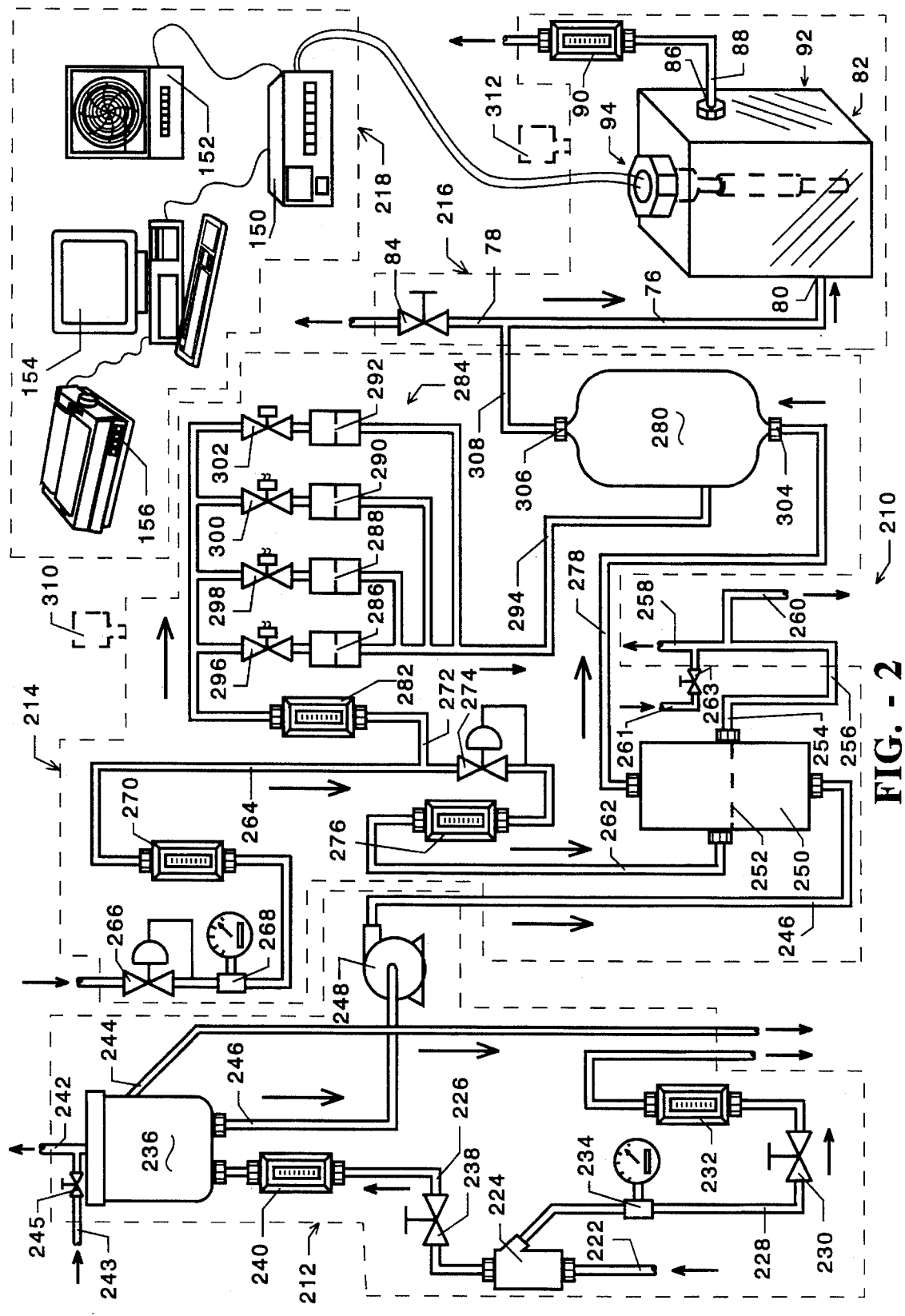
FIG. 2 is a schematic diagram of an analyzer embodying the principals of the present invention which is designed for sampling a chemical process liquid stream.

FIG. 2 shows a schematic diagram of an analyzer 210 specifically adapted for detecting water in organic liquids. This analyzer 210 utilizes a sampling means 212 for providing a sample of a process liquid, conditioning and diluting means 214 for conditioning the sample for sampling and diluting it, moisture detecting means 216, and control and output means 218 for controlling the operation of the analyzer and converting the signals from the detecting means 216 into output data.

The liquid to be sampled enters the sampling means 212 of the analyzer 210 through an input line 222 which is attached to a source of the liquid stream to be sampled. The sample may be taken from any convenient location in the chemical process stream where the determination of the water content is of interest. The input line 222 is connected to a filter 224 such as a Y-strainer which serves to remove any solid particles from the incoming liquid sample. The filter 224 is similar to that used in the detector shown in FIG. 1 in that in may be of any appropriate type which is capable of preventing passage of solid particles into the liquid sample incoming flow line 226. A relatively large portion of the incoming liquid to the filter 224 is returned unfiltered back to a low pressure point in the chemical process stream through a liquid return line 228. A flow restrictor 230 is provided in the liquid return line 228 with a flow meter 232 positioned in the line 228 downstream of the restrictor 230 and a pressure gauge 234 positioned in the line 228 upstream of the restrictor 230. The flow restrictor 230 may be of any suitable type capable of controlling the flow of the liquid therethrough and thus the pressure of the liquid upstream of the restrictor. A needle-type flow restricting valve is an example of a suitable type of restrictor 230. The pressure gauge 234 and flow restrictor 230 provide a means to monitor and control the pressure of the sample passing through line 228 while the flowmeter 232 serves to verify movement of the liquid through the line 228.

The filtered liquid sample leaves the filter 224 through the incoming flow line 226 where it passes to an overflow vessel 236. The incoming flow line 226 from the filter 224 to the overflow vessel 236 has a flow restrictor 238 therein, similar to flow restrictor 230, and a flow meter 240 downstream thereof as shown in FIG. 2. The flow restrictor 238 and flow meter 240 are used to control and monitor the flow of the liquid sample to the overflow vessel 236.

The top of the overflow vessel 236 is provided with a vent line 242 to the atmosphere or a plant scrubber to allow any gasses which may arrive into the system to escape permitting free flow of the liquid sample into the overflow vessel 236. An overflow line 244 is connected to the side of the overflow vessel 236 so that when the sample level in the overflow vessel 236 reaches the level at which the line 244 connects to the vessel 236, the excess liquid will exit the vessel through that line 244. The overflow line 244 is connected to a low pressure point in the chemical process so that the excess liquid is discharged back into the process. A small stream of dry gas such as dry nitrogen or dry air is fed from a suitable source through a line 243 and a pressure regulator 245 to the line vent line 242 in which it escapes to the atmosphere or plant scrubber. The dry gas prevents moisture from atmospheric air from entering the overflow vessel 236 and contaminating the liquid sample therein and also preventing moisture from passing through line 244 back to the process.

The bottom of the overflow vessel 236 has a liquid sample incoming flow line 246 connected thereto through which the liquid sample passes from the over flow vessel 236 into the conditioning and dilution means 214 of the analyzer 210. If the viscosity of the liquid sample is too high for easy flow through the line 246, the line 246 may be provided with a metering pump 248 to aid in the flow of the liquid to the conditioning and diluting means 214.

The conditioning and dilution means 214 includes a head space vessel 250 at the bottom of which is connected the incoming flow line 246 from the overflow vessel 236. The head space vessel 250 serves to maintain the water molecules in the liquid sample stream in equilibrium with the water molecules above the liquid stream. The liquid sample in the head space vessel 250 is constantly renewed during operation. Fresh liquid sample is constantly fed into the vessel 250 from the incoming flow line 246. The liquid sample rises in the vessel 250 until it reaches the level indicated by the dashed line 252, which is the level of the opening in the vessel 250 to which the return line 254 is connected, and continuously exits through the return line 254. The return line 254 contains a U-shaped trap portion 256 to seal the vessel 250 from escape of gas through the opening to the line 254. The line 254, after the trap portion 256, splits into two separate lines 258 and 260. Line 258 is vented to the atmosphere or plant scrubber, while line 260 is connected to the process stream at a low pressure point to provide a return to the process for the excess liquid. A small stream of dry gas such as dry nitrogen or dry air is fed from a suitable source through a line 261 and a pressure regulator 263 to the line vent line 258 in which it escapes to the atmosphere or plant scrubber. This dry gas prevents moisture from entering the vent 258 and contaminating the liquid.

A water-free fluid, preferably a dry gas such as dry nitrogen or dry air is introduced into the head space vessel 250 by means of a dry gas line 262, connected at one end to the head space vessel 250 at a point above the level 252 of the liquid sample and at the other end to a main incoming dry gas line 264. The main incoming dry gas line 264 is connected at its incoming end to a suitable source of the water-free fluid such as a dry gas as explained above in connection with the analyzer of FIG. 1. This source of dry gas may also be used to supply the dry gas to the lines 243 and 261. The dry gas line 264 includes a pressure regulator 266, and a pressure gauge 268 and flow meter 270, both downstream of the pressure regulator 266. The pressure regulator 266 serves to control the pressure of the incoming dry gas while the pressure gauge 268 and flow meter 270 provide a means to monitor the gas pressure and flow respectively of the incoming dry gas. After the flow meter 270, the main dry gas line 264 splits into two separate lines, the dry gas line 262 and a diluent dry gas line 272. The dry gas line 262 to the head space vessel 250 has a flow controller 274 positioned therein, downstream of the branch of the diluent gas line 272. A flow meter 276 is positioned in the gas line 262 downstream of the flow controller 274. The flow controller 274 assures that a constant flow rate of dry gas is supplied to the head space vessel 250 regardless of variations in pressure or flow upstream of the controller due to flow through the diluent gas line 272.

The dry gas enters the head space vessel 250 from the dry gas line 262 above the level 252 of the liquid sample therein and sweeps across the surface of the liquid sample picking up the water molecules above the liquid sample which are in equilibrium with the water molecules in the liquid sample. The dry gas carries the water molecules out through the top of the head space vessel 250 and through line 278 to a mixing chamber 280. The amount of water in the gas leaving the head space vessel 250 through the line 278 is proportional to the amount of water in the liquid sample.

The diluent dry gas line 272 carries a flow of dry gas from the main dry gas line 264 through a flow meter 282 to a computer-selective dry gas variable flow rate path network 284. The dry gas variable flow rate path network 284 comprises a series of flow restrictors such as orifices 286, 288, 290 and 292, each of which is of a different size whereby the flow rate of dry gas through each of the orifices 286, 288, 290 and 292 is different. The orifices 286, 288, 290 and 292 are located in parallel between the incoming dry gas line 272 and a gas line 294 to the mixing chamber 280.

An on-off valve 296, 298, 300, and 302 is associated with each of the orifices 286, 288, 290 and 292 respectively. The valves 296, 298, 300 and 302 are connected between the line 272 and their respective orifices 286, 288, 290 and 292 such that the gas from line 272 must pass through one of the valves 296, 298, 300 or 302 and its associated orifice 286, 288, 290 or 292 before passing to the gas line 294 to the mixing chamber 280. Each of the valves 296, 298, 300 and 302 may be any suitable type of an electrically actuated on-off valve such as a solenoid actuated, pneumatically operated valve, the operation of which is controlled by electrical signals from the control and output means 218.

The line 294 from the variable flow rate path network 284 is connected to an inlet in the side of the mixing chamber 280. The line 278 from the head space vessel 250 is connected to an inlet 304 at the bottom of the mixing chamber 280 so that incoming water containing gas from the head space vessel 250 and the dry gas from the variable flow rate path network 284 meet in the mixing chamber 280 and are mixed. The mixing chamber 280 allows the two gas streams to mix uniformly with the result that the dry gas dilutes the gas from the head space vessel 250 and lowers the water content of the resulting sample stream.

After mixing in the mixing chamber 280, the resulting gas sample stream exits the mixing chamber 280 through an outlet 306 to which is connected one end of a sample flow line 308 for flow to the moisture detecting means 216. The moisture detecting means 216 is the same as that previously described in connection with the analyzer of FIG. 1, and includes the sample input line 76 and the vent line 78 to which the other end of the sample flow line 308 is connected. As in case of the device of FIG. 1, the sample input line 76 is connected to the inlet 80 of the moisture detecting cell 82. The vent line 78 is vented to the atmosphere or plant scrubber through an adjustable flow restrictor 84 which serves to provide a back pressure in the system allowing for greater control of the flow of the gas sample through the input line 76 and into the moisture detecting cell 82. The moisture detecting cell 82 used in connection with the analyzer of FIG. 3 is of the same type as used in connection with the analyzer of FIG. 1 and is shown and described in connection with FIG. 2. The outlet 86 of the moisture detecting cell 82 has a vent line 88 connected thereto which is vented to the atmosphere or plant scrubber through a flow meter 90. The flow meter 90 is used to monitor the flow of the sample through the moisture detecting cell 82.

An electrolysis current produced in the cell 82 is proportional to the water in the gas sample passing through the cell 82, and is carried by a pair of lead wires 124 and 126 to the control and output means 218. The control and output means 218, as in the case of the analyzer of FIG. 1, may include a controller-microprocessor unit 150 to which the lead wires 124 and 126 are connected for converting the current signal from the cell 82 for output to a recorder 152 such as a chart recorder. The control and output means may also include the computer 154 connected to the controller-microprocessor unit 150 and a printer 156.

As in the case of the analyzer shown in FIG. 1, the conditioning and dilution means 214, including the head space vessel 250, the variable flow rate path network 284, mixing chamber 280 and associated piping, and the moisture detecting means 216, including the moisture detecting cell 82 and its associating piping, are each housed in a thermostated unit, or together in a single thermostated unit. The thermostated units serve to maintain the sample and dry gas passing though the conditioning and dilution means 214 and moisture detecting means 216 at a constant temperature. The units may be thermostated by the use of hot air heaters shown schematically at 310 and 312, although other types of heaters such as electrical heaters or the like may be used. By maintaining a constant temperature, variations in flow of the sample and the dry gas due to variations in the temperature will be prevented.

In the operation of the device of FIG. 2, which is designed for the monitoring of water in an organic liquid stream, the incoming liquid sample is filtered by the filter 224 and passes into the overflow vessel 236. A stream of the liquid sample flows from the overflow vessel 236 to the head space vessel 250 in which molecules of water leave the liquid solution and reach an equilibrium with the water molecules in the liquid. Thus the head space vessel 250 extracts a proportional amount of water molecules from the liquid sample. The dry gas entering the head space vessel 250 from the line 262 sweeps across the surface of the liquid sample in the vessel 150 and picks up the water molecules and carries them to the mixing chamber 280.

Dry gas is fed to the mixing chamber 280 through the flow rate varying network 284. The flow rate varying network 284 provides the proper flow rate of the dry gas to the mixing chamber 280 to provide for the desired dilution of the sample in the mixing chamber 280. In the network 284, the dry gas passes through one of the valves 296, 298, 300 or 302 and its associated orifice 286, 288, 290 or 292 as determined by the control and output means 218 to provide the desired flow rate of the dry gas to the mixing and diluting mixing chamber 280. In the mixing chamber 280, the gas stream from the head space vessel 250 containing the water molecules is mixed with a the dry gas which is supplied to the mixing chamber 280 through one of the orifices 286, 288, 290 or 292 at a known flow rate. Thus, as the flow rates to the diluting mixing chamber 280 of both the water containing stream from the head space vessel 250 and the diluent dry gas are known, the amount of dilution of the sample stream by the dry gas is known.

The resulting diluted sample stream leaves the mixing chamber 280 and passes through lines 308 and 76 and enters the moisture detecting cell 82. The diluted sample stream passes into the cell 82, bathing the electrode area 144 thereof. Any water in the sample reacts with the phosphorous pentoxide film as described above, producing a current proportional to the amount of water reacting with the film. The current signal is carried to the controller-microprocessor unit 150 by the lead wire 124 and 126 where the signal is converted to a form for outputting to the recorder 152 and computer 154 for further processing.

Assuming that the valves 296, 298, 300 and 302 of the flow rate varying network 284 are set so that the valve 302, associated with the smallest orifice 292 is open, with the other valves closed, the flow rate of the dry diluting gas supplied to the mixing chamber 280 will be at its lowest flow rate and the sample stream leaving the mixing chamber 280 will have the least amount of dilution by the dry gas. If the controller-microprocessor unit 150 receives a signal from the moisture detection cell 82 that is incapable of being converted into a reading of the water content because the water content of the sample flow through the cell 82 is too high, the controller-microprocessor unit 150 will cause one of the other valves 296, 298 or 300 to open and valve 302 to close, permitting the dry gas to flow through an orifice of greater diameter and increasing the flow of the diluting dry gas to the mixing chamber 280. With an increased flow rate of the dry diluting gas to the mixing chamber 280, when such increased flow is then mixed with the same constant flow of the gas containing the water molecules from the head space vessel 250, the sample stream from the head space vessel is further diluted and the water content of the resulting stream is lowered. As the orifices 286, 288, 290 and 292 are of decreasing size, thus providing for a increasing amount of flow of the dry gas to the mixing chamber 280 by opening the valve to an orifice of a larger diameter and closing the others, the controller-microprocessor unit 150 can provide for the proper path through the variable flow path network 284. This will provide the proper flow rate of the dry gas to the mixing-chamber 280 so that when the gas stream from the head space vessel 250 is diluted, the water content of the resulting mixture is within a range that can be accurately detected by the moisture detection cell 82. The computer 154 may be programmed so that the proportion of dry gas to gas containing the molecules of water is known for each flow path (orifice) through the network 284 so the actual concentration of water in the vapor stream can be calculated using the proper sample dilution factor.

The analyzer 210 may be calibrated by using a laboratory sample of liquid having a known water content and using the flow path for the diluent dry gas which passes through the orifice 292 providing the smallest flow rate therethrough. The flow rates of the liquid sample and dry gas to the head space vessel 250 are set at a constant rate. By way of example, the flow rate of the liquid sample to the head space vessel 250 may be 6.9 ml/min and the flow rate of the dry gas to the head space vessel 250 may be 100 ml/min. The flow rate of the dry gas containing the water molecules from the head space vessel 250 to the mixing vessel 280 will also be 100 ml/min. The smallest orifice 292 has a size such that the pressure regulator 266 can be adjusted to set the flow rate of the diluent dry gas through the orifice 292 to the mixing vessel at 1125 ml/min, resulting in a flow rate through the moisture detecting cell 82 of the combined diluent dry gas and dry gas containing the water molecules of 1225 ml/min.

With the analyzer 210 calibrated to provide an accurate readout of the moisture content with the flow of the diluent dry gas through the smallest orifice 292, the computer 154 may be programmed with an appropriate factor to provide for an accurate readout when the other orifices 290, 288 and 286 are used. For example, the second smallest orifice 288 may provide for a diluent dry gas flow rate of 2250 ml/min, the third smallest orifice 288 for a sample flow rate of 4500 ml/min and the largest orifice 50 for a flow rate of 6750 ml/min, resulting in flow rates through the moisture detecting cell 82 of the combined diluent dry gas and dry gas from the head space vessel 250 containing the water molecules of 2350 ml/min, 4600 mil/min and 6850 ml/min respectively. With these flow rates, the computer 154 may be programmed to multiply the output from the moisture detecting cell 82 by a factor of 2, 4, or 6 depending upon whether orifice 290, 288 or 286, respectively, is being used, to calculate the exact moisture content of the sample.

With the arrangement as described, the analyzer 210 can accurately detect moisture content in a liquid sample of up to 500 ppm when there is flow of the diluent dry gas through the smallest orifice 292, up to 1000 ppm when there is flow of the diluent dry gas through the second smallest orifice 280, up to 2000 ppm with flow through the third smallest orifice 288 and up to 3000 ppm when there is flow of the diluent dry gas is directed through the largest orifice 286. The computer is programmed so that the orifice selected is the one which will result in the least dilution, but still permit an accurate reading by the moisture detecting cell 82. This will ensure that the most sensitive scale will be used resulting in the most precise measurements for a given water concentration.

While the invention has been described above with reference to specific embodiments thereof, it is apparent that many changes, modifications, and variations can be made without departing from the concepts disclosed herein. Accordingly, it is intended to embrace all such changes, modifications, and variations that fall within the scope of the appended claims.

What is claimed is:

1. An analyzer for detecting and measuring water content of a said sample comprising:
   a. means for gathering a stream of the fluid sample,
   b. diluting means for diluting the sample with a water-free fluid, and
   c. moisture detection means for detecting the presence of water in the diluted sample and providing an electrical signal indicative of the amount of water in the sample, wherein said diluting means dilutes the sample with a dry gas.

2. The analyzer of claim 1 further including means for maintaining said diluting means and said moisture detecting means at a constant temperature.

3. The analyzer of claim 1 wherein said diluting means includes a mixing means for mixing and diluting the fluid sample with said dry gas.

4. The analyzer of claim 1 wherein said diluting means includes means for selectively varying the amount of dilution of said sample.

5. The analyzer of claim 4 further including computer means for controlling the means for selectively varying the amount of dilution of said sample to initiate a change in the amount of dilution of the sample and for calculating the actual water content of the sample in response to the electrical signal received from said moisture detection means.

6. The analyzer of claim 3 wherein said fluid sample is a gas, said diluting means including means for varying a flow rate of the gas sample to the mixing means to vary the amount of dilution of the gas sample by the dry gas and thus the vary the amount of water in the resulting diluted sample.

7. The analyzer of claim 6 wherein said means for varying the flow rate of the gas sample includes a plurality of different size orifices and valve means for passing said gas sample through a selected one of said different size orifices before the gas sample reaches said mixing means to selectively vary the flow rate of the gas sample to the mixing means.

8. The analyzer of claim 7 further including means for maintaining the flow rate of said dry gas to said mixing means constant.

9. The analyzer of claim 8 further including means for maintaining said diluting means and said moisture detecting means at a constant temperature.

10. The analyzer of claim 1 wherein said fluid sample is a liquid, said analyzer further comprising a head space vessel for extracting water molecules from the liquid sample stream and maintaining the water molecules above said liquid sample in equilibrium with the molecules in the liquid sample and means for providing a dry gas for carrying away said water molecules above said solution, said diluting means including mixing means for mixing and diluting the gas carrying the water molecules with a diluent dry gas to provide a diluted sample, and means for passing said diluted sample to said moisture detection means.

11. The analyzer of claim 10, wherein said diluting means further includes means for varying a flow rate of the diluent dry gas to the mixing means to vary the amount of dilution of the dry gas carrying said water molecules whereby the water content in the resulting diluted sample may be varied.

12. The analyzer of claim 11 wherein said means for varying the flow rate of the diluent dry gas includes a plurality of different size orifices and valve means for passing said diluent dry gas through a selected one of said different size orifices before the diluent dry gas reaches said mixing means to selectively vary the flow rate of the diluent dry gas to the mixing means.

13. The analyzer of claim 12 further including means for maintaining the flow rate of said dry gas carrying said water molecules to said mixing means constant.

14. The analyzer of claim 13 further including means for maintaining said diluting means and said moisture detecting means at a constant temperature.

15. The analyzer of claim 10 wherein said head space vessel includes an outlet and a return line connected to said outlet for returning the liquid sample passing therethrough back to its source, said return line having a trap therein for providing a liquid sample seal between the interior of the head space vessel and the downstream side of the return line.

16. The analyzer of claim 15 further including an overflow vessel for receiving said liquid sample from a source, and means for returning the overflow from the overflow vessel back to its source and passing a portion of said liquid sample in said overflow vessel to said diluting means.

17. The analyzer of claim 16 wherein said overflow vessel and said trap in said return line of said head space vessel each have a vent associated therewith, and further including means for passing a dry gas through said vents to prevent moisture from the atmosphere from entering the said vents.

18. A method for detecting and measuring water content in a fluid sample comprising:
   a) providing a stream of a fluid sample,
   b) diluting the stream of fluid sample with a water-free fluid to provide a diluted sample, and
   c) detecting the presence of water in the fluid sample by means of a moisture detector, and providing an electrical signal to indicate a total amount of water in the sample, wherein said water-free fluid is a dry gas.

19. The method of claim 18 further including maintaining said diluting means and said moisture detecting means at a constant temperature.

20. The method of claim 18 wherein said fluid sample is a gas, said method including mixing and diluting the gas sample with a dry gas in a mixing means and passing the resulting diluted sample stream to said moisture detector, a flow rate of the gas sample to the mixing means being able to be varied to vary the amount of dilution of the gas sample by the dry gas and thus vary the amount of water in the resulting sample being detected by the moisture detector.

21. The method of claim 20 further including varying the flow rate of the gas sample by selectively activating valve means to pass said gas sample through a selected one of a plurality of different size orifices before the gas sample reaches said mixing means to selectively vary the flow rate of the gas sample to the mixing means.

22. The method of claim 21 further including maintaining the flow rate of said dry gas to said mixing means constant.

23. The method of claim 22 further including maintaining said diluting means and said moisture detecting means at a constant temperature.

24. The method of claim 18 wherein said fluid sample is a liquid, said method further comprising passing said liquid sample to a head space vessel and extracting water molecules from the liquid sample and maintaining such water molecules in equilibrium with the water molecules in the sample, providing a dry gas to carry the water molecules above said liquid solution to a mixing and diluting means, diluting said dry gas containing said water molecules with a diluent dry gas in said mixing and diluting means to from a diluted sample, and passing the diluted sample to said a moisture detector.

25. The method of claim 24 wherein a flow rate of the diluent dry gas to the mixing and diluting means may be varied to vary the amount of dilution of the gas containing the water molecules and thus vary the concentration of water in the resulting diluted sample.

26. The method of claim 25 further including varying the flow rate of the diluent dry gas by selectively actuating valve means to pass said diluent dry gas through a selected one of a plurality of different size orifices before the diluent dry gas reaches said mixing means to selectively vary the flow rate of the diluent dry gas to the mixing means.

27. The method of claim 26 further including maintaining the flow rate of said dry gas carrying said water molecules to said mixing means constant.

28. The analyzer of claim 27 further including maintaining said diluting means and said moisture detecting means at a constant temperature.

* * * * *